United States Patent
Tavernelli et al.

(10) Patent No.: US 11,942,192 B2
(45) Date of Patent: Mar. 26, 2024

(54) DENSITY-FUNCTIONAL THEORY DETERMINATIONS USING A QUANTUM COMPUTING SYSTEM

(71) Applicant: International Business Machines Corporation, Armonk, NY (US)

(72) Inventors: Ivano Tavernelli, Zurich (CH); Panagiotis Barkoutsos, Zurich (CH); Pauline Ollitrault, Zurich (CH); Max Rossmannek, Zurich (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 868 days.

(21) Appl. No.: 16/927,533

(22) Filed: Jul. 13, 2020

(65) Prior Publication Data

US 2022/0012382 A1   Jan. 13, 2022

(51) Int. Cl.
| | |
|---|---|
| *G01N 33/48* | (2006.01) |
| *G01N 33/50* | (2006.01) |
| *G06N 10/00* | (2022.01) |
| *G16C 10/00* | (2019.01) |
| *G16C 20/50* | (2019.01) |

(52) U.S. Cl.
CPC ............ G16C 20/50 (2019.02); G06N 10/00 (2019.01); G16C 10/00 (2019.02)

(58) Field of Classification Search
CPC ......... G16C 20/50; G16C 10/00; G06N 10/00
See application file for complete search history.

(56) References Cited

U.S. PATENT DOCUMENTS

| | | |
|---|---|---|
| 8,301,390 B2 | 10/2012 | Sastry et al. |
| 2007/0043545 A1 | 2/2007 | Yonezawa et al. |
| 2007/0239366 A1 | 10/2007 | Hilton et al. |
| 2009/0182542 A9* | 7/2009 | Hilton ............... B82Y 10/00 703/11 |
| 2015/0142398 A1 | 5/2015 | Miller, III et al. |

(Continued)

FOREIGN PATENT DOCUMENTS

EP    2599141 B1    12/2019

OTHER PUBLICATIONS

Wesolowski et al. Ab initio free energy perturbation calculations of solvation free energy using the frozen density functional approach. Journal of Physical Chemistry, vol. 98, pp. 5183-5187. (Year: 1994).*

(Continued)

*Primary Examiner* — Russell S Negin
(74) *Attorney, Agent, or Firm* — Amin, Turocy & Watson, LLP

(57) ABSTRACT

Techniques facilitating density-functional theory determinations using a quantum computing system are provided. A system can comprise a first computing processor and a second computing processor. The first computing processor can generate a density-functional theory determination. The second computing processor can input a quantum density into the density-functional theory determination. The first computing processor can be operatively coupled to the second computing processor. Further, the first computing processor can be a classical computer and the second computing processor can be a quantum computer.

25 Claims, 13 Drawing Sheets
(4 of 13 Drawing Sheet(s) Filed in Color)

(56) References Cited

U.S. PATENT DOCUMENTS

2018/0096085 A1 4/2018 Rubin
2020/0057957 A1 2/2020 Johnson et al.

OTHER PUBLICATIONS

Hatcher et al., "A Method to Calculate Correlation for Density Functional Theory on a Quantum Processor" Advanced Logic Laboratory, Samsung Semiconductor Inc. 12 pages, Mar. 13, 2019.
Hedegard et al., "Density Matrix Renormalization Group with Efficient Dynamical Electron Correlation Through Range Separation" arXiv:1502.06157v2 (May 28, 2015). 29 pages.
Barkoutsos et al., "Quantum algorithms for electronic structure calculations: particle/ hole Hamiltonian and optimized wavefunction expansions" arXiv:1805.04340v1 (May 14, 2018) 14 pages.
Takeshita et al., "Increasing the Representation Accuracy of Quantum Simulations of Chemistry without Extra Quantum Resources" Physical Review X 10, 011004 (Jan. 7, 2020) 9 pages.
"Heme" Wikipedia Article. last web accessed Apr. 8, 2020. https://en.wikipedia.org/wiki/Heme.
Rossmannek et al., "Quantum HF/DFT-Embedding Algorithms for Electronic Structure Calculations: Scaling up to Complex Molecular Systems", arXiv:2009.01872v1 [quant-ph], Sep. 3, 2020, 16 pages.
Ma et al., "Quantum simulations of materials on near-term quantum computers", vol. 6, No. 1, Jul. 2, 2020, 8 pages.
Knizia et al., "Density matrix embedding: A simple alternative to dynamical mean-field theory" Physical Review Letters, vol. 109, No. 18, Nov. 2, 2012, 5 pages.
Petras et al., "Fully quantum embedding with density functional theory for full configuration interaction quantum Monte Carlo", arxiv.org, Cornell University Library, Jun. 9, 2019, 36 pages.
Halbert et al., "Investigating solvent effects on the magnetic properties of molybdate ions ($MoO_4^{2-}$) with relativistic embedding". arXiv:1912.06192v2 [physics.chem-ph], May 20, 2020, 17 pages.
International Search Report and Written Opinion received for PCT Application Serial No. PCT/EP2021/069346 dated Oct. 26, 2021, 12 pages.
Response to the communication received for European Patent Application Serial No. 21748808.9 dated Aug. 21, 2023, 3 pages.
Examination Report No. 1 received for Australian Patent Application Serial No. 2021307910 dated Dec. 19, 2023, 4 pages.

* cited by examiner

DENSITY-FUNCTIONAL THEORY DETERMINATIONS USING A QUANTUM COMPUTING SYSTEM

BACKGROUND

The subject disclosure relates to quantum computing and, more specifically, to facilitating density-functional theory determinations using a quantum computing system. Simulations of large molecules utilizing classical computers (e.g., non-quantum computers) are intractable because of the exponential growth of the Hilbert space. Quantum simulations of large molecules are a possible solution because they can represent this exponential Hilbert space efficiently using qubits. However, quantum simulations of molecular systems are limited to very small sizes because of limited coherence time, gate noise, and other complexities.

For example, Yonezawa et al. (U.S. Patent Application Publication No. 2007/0043545) discusses "dividing a molecule or a part of molecule to be simulated into a [Quantum Mechanics] QM space and an [Molecular Mechanics] MM [space] and applying an ab initio molecular orbital method to the QM space." See Abstract. Yonezawa et al., however, uses only a classical processor and, therefore, is limited in the size of a molecular system that can be analyzed.

In another example, Rubin (U.S. Patent Application Publication No. 2018/0096085) discusses "quantum computations executed on one or more quantum processor units (QPUs), which may operate in parallel, are used for density matrix embedding calculations." See paragraph [0012]. In Rubin, "quantum processor units (QPUs) are used to compute reduced density matrices (RDMs)." See paragraph [0055]. Rubin discusses that "1-reduced density matrix (1-RDM) and 2-reduced density matrix (2-RDM) are computed for each fragment based on the embedded Hamiltonian for the fragment." See id. The reduced density matrix of Rubin, however, lacks the ability to provide a rigorous iterative density functional theory-based embedding for quantum computing calculations.

SUMMARY

The following presents a summary to provide a basic understanding of one or more embodiments of the invention. This summary is not intended to identify key or critical elements or delineate any scope of the particular embodiments or any scope of the claims. Its sole purpose is to present concepts in a simplified form as a prelude to the more detailed description that is presented later. In one or more embodiments described herein, systems, computer-implemented methods, apparatuses, circuits, and/or computer program products that facilitate density-functional theory determinations using a quantum computing system are provided.

According to an embodiment, a circuit can comprise a first computing processor that generates a density-functional theory determination. The circuit also can comprise a second computing processor that inputs a quantum density into the density-functional theory determination generated by the first computing processor. The first computing processor can be operatively coupled to the second computing processor. An advantage of such a circuit is reduction of the quantity of qubits used by the circuit.

According to another embodiment, a computer-implemented method can comprise generating, by a first computing processor of a system, a density-functional theory determination. The method can also comprise inputting, by a second computing processor of the system, a quantum density into the density-functional theory determination. The first computing processor can be operatively coupled to the second computing processor. An advantage of such a computer-implemented method is that the number of qubits necessary can be reduced because a portion of active electrons (e.g., valence electrons) are replaced by the first computing processor that performs the density-functional theory determination.

Another embodiment relates to a system that can comprise a first computing processor that generates a density-functional theory determination. The system also can comprise a second computing processor that inputs a quantum density into the density-functional theory determination. The first computing processor can be operatively coupled to the second computing processor. An advantage of such a system is that the quantity of qubits used by the circuit can be reduced through utilization of the first computing processor to generate the density-functional theory determination.

According to a further embodiment, provided is a computer-implemented method that can comprise employing, by a device operatively coupled to a processor, a first computing processor to implement a density-functional theory determination. The method also can comprise employing, by the device, a second computing processor to update the density-functional theory determination, resulting in an updated density-functional theory determination. Further, the method can comprise employing, by the device, the first computing processor to reoptimize the updated density-functional theory determination based on iterative density-functional theory-based embedding for quantum computing determinations. An advantage of such a computer-implemented method is a rigorous iterative density-functional theory-based embedding for quantum computing calculations.

Yet another embodiment relates to a device that can comprise a first computing processor that implements a density-functional theory determination and a second computing processor that updates the density-functional theory determination, resulting in an updated density-functional theory determination. The first computing processor reoptimizes the updated density-functional theory determination based on iterative density-functional theory-based embedding for quantum computing determinations. An advantage of such a device is that a rigorous iterative density-functional theory-based embedding for quantum computing calculations can be achieved.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details.

Figure 1:
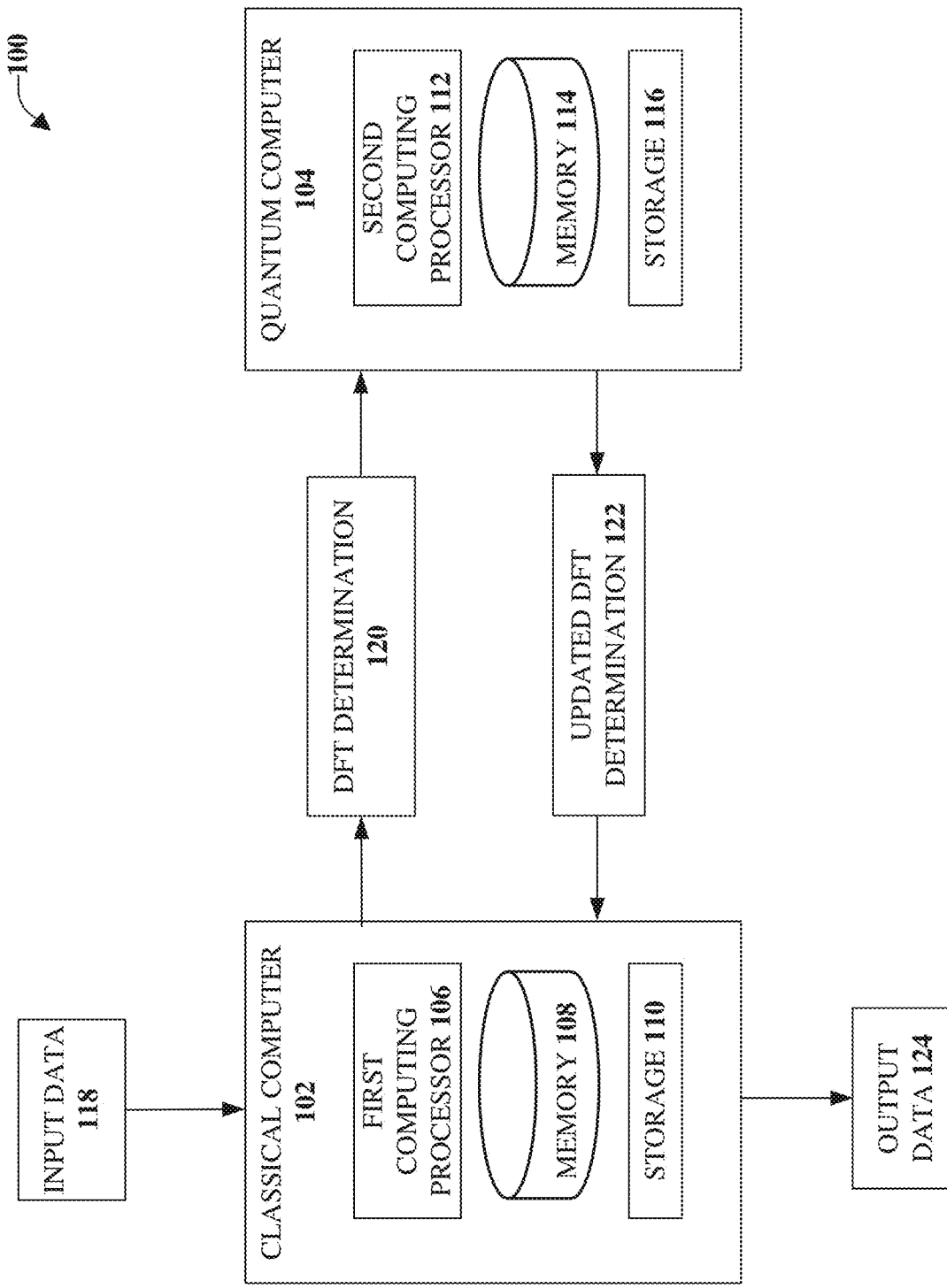
FIG. 1 illustrates a block diagram of an example, non-limiting, system that facilitates density-functional theory determinations using a hybrid quantum and classical computing processor in accordance with one or more embodiments described herein.

FIG. 1 illustrates a block diagram of an example, non-limiting, system 100 that facilitates density-functional theory determinations using a hybrid quantum and classical computing processor in accordance with one or more embodiments described herein. Aspects of systems (e.g., the system 100 and the like), apparatuses, or processes explained in this disclosure can constitute machine-executable component(s) embodied within machine(s), e.g., embodied in one or more computer readable mediums (or media) associated with one or more machines. Such component(s), when executed by the one or more machines, e.g., computer(s), computing device(s), virtual machine(s), etc. can cause the machine(s) to perform the operations described.

In various embodiments, the system 100 can be and/or can include any type of component, machine, device, facility, apparatus, and/or instrument that comprises a processor and/or can be capable of effective and/or operative communication with a wired and/or wireless network. Components, machines, apparatuses, devices, facilities, and/or instrumentalities that can comprise the system 100 can include tablet computing devices, handheld devices, server class computing machines and/or databases, laptop computers, notebook computers, desktop computers, cell phones, smart phones, consumer appliances and/or instrumentation, industrial and/or commercial devices, hand-held devices, digital assistants, multimedia Internet enabled phones, multimedia players, and the like.

In various embodiments, the system 100 can be a computing system associated with technologies such as, but not limited to, quantum computing technologies, classical computing technologies, circuit technologies, processor technologies, computing technologies, artificial intelligence technologies, chemical technologies, simulation technologies, medicine and materials technologies, supply chain and logistics technologies, financial services technologies, and/or other digital technologies. The system 100 can employ hardware and/or software to solve problems that are highly technical in nature (e.g., first portions of a simulation are performed on a classical processor due to the less-complex nature of those portions of the simulation and second portions of the simulation are performed on a quantum processor due to the complex nature of those portions of the simulation). Accordingly, not all portions of the simulation need to be performed on the quantum processor, which is a benefit because the number of qubits needed for the simulation can be reduced.

Further, in certain embodiments, some of the processes performed can be performed by one or more specialized computers (e.g., one or more specialized processing units, a specialized computer with a coupling component, a feedback component, and so on) to carry out defined tasks related to density-functional theory determinations using a quantum computing system.

The system 100 and/or components of the system 100 can be employed to solve new problems that arise through advancements in technologies, computer architecture, and/or the like. The system 100 (and other embodiments discussed herein) can use an iterative hybrid classical computing and quantum computing approach to perform simulations of large molecules or other items. One or more embodiments of the system 100 can provide technical improvements to computing systems, classical computing systems, quantum computing systems, circuit systems, processor systems, artificial intelligence systems, deep learning computing systems, and/or other systems.

In the embodiment shown in FIG. 1, the system 100 can comprise a classical computer 102 and a quantum computer 104. The classical computer 102 can comprise a first computing processor 106, a first memory 108, and first storage 110. The quantum computer 104 can comprise a second computing processor 112, a second memory 114, and a second storage 116. The memories (e.g., the first memory 108, the second memory 114) can store computer executable components and instructions. The processors (e.g., the first computing processor 106, the second computing processor 112) can facilitate execution of instructions (e.g., computer executable components and corresponding instructions) via the classical computer 102 and the quantum computer 104. The classical computer 102 and the quantum computer 104 can be electrically, communicatively, and/or operatively coupled to one another to perform one or more functions of the system 100.

The various embodiments provided herein can facilitate density-functional theory determinations using a quantum computing system coupled with a classical computing system. A problem related to simulations of large molecules utilizing classical computers (e.g., non-quantum computers) is that such simulations are intractable because of the exponential growth of the Hilbert space. The Hilbert space is a mathematical concept or an abstract vector space that can possess the structure of an inner product that allows length and angle to be measured. Quantum simulations of large molecules are a possible solution because they can represent this exponential Hilbert space efficiently using qubits. However, quantum simulations of molecular systems are usually limited to very small sizes because of limited coherence time, gate noise, and other complexities. The problems associated with the limitation related to the size of the molecular systems that can be simulated is solved by the disclosed aspects and large sized molecular systems can be simulated as discussed herein.

The first computing processor 106 can be employed to implement a density-functional theory determination. For example, input data 118 can be provided to the first computing processor 106. The input data 118 can be, for example, at least a portion of a molecular system being analyzed. The first computing processor 106 can perform the density-functional theory determination on one or more portions of the input data 118 and can output (e.g., as output data) a result of the density-functional theory determination 120.

The result of the density-functional theory determination 120 can be input data received at the second computing processor 112. For example, based on the result of the density-functional theory determination 120, the second computing processor 112 can update the result of the density-functional theory determination. This can produce an updated density-functional theory determination 122, which is output (as output data) by the second computing processor 112. The updated density-functional theory determination 122 is returned to the first computing processor 106 (as input data) (via, for example, a feedback component, not shown).

Accordingly, the first computing processor 106 can be employed to reoptimize the updated density-functional theory determination 122 from the second computing processor 112 based on iterative density-functional theory-based embedding for quantum computing determinations. The reoptimized updated density-functional theory determination is passed to the second computing processor. The second computing processor receives the reoptimized updated density-functional theory determination and performs another update. It is to be understood that the density-functional theory determination performed by the first computing processor 106 and the update to the density-functional theory determination performed by the second computing processor 112 can be recursive or iterative. For example, the density-functional theory determination can be updated (by the second computing processor 112) and reoptimized (by the first computing processor 106) iteratively until a final determination or a final result is reached and output as output data 124. It is noted that the input data 118 is illustrated from being received externally from the classical computer 102. However, the disclosed aspects are not limited to this implementation and the input data 118 can be provided by the classical computer 102.

The first computing processor 106 can be a classical computing processor and the second computing processor 112 can be a quantum computing processor. By utilizing a classical computing processor to implement (and/or reimplement) the density-functional theory determination, the number of qubits utilized by the system 100 can be reduced.

It is to be appreciated that the system 100 (and other embodiments discussed herein) provides a technical improvement related to simulating molecular systems of sizes which are not possible to be simulated on classical computers at the same level of accuracy. To accommodate the current limitations of quantum computing, the number of qubits and depth of the circuits can be minimized as discussed herein. However, the number of qubits and depth of the circuits can be increased based on increasing capabilities of quantum computing. For example, Effective Core Potentials (ECP) can allow the removal of the atomic core electrons. For example, ECPs are a useful way to replace the core electrons in a calculation with an effective potential, thereby eliminating the need for core basis functions, which usually require a large set of Gaussians to describe the core basis functions. By means of active space embedding it is possible to freeze a subset of the molecular orbitals of a system; the remaining (unfrozen) set is referred to as the active space.

Accordingly, the disclosed aspects can help a processor to determine and provide results faster and with less computing resources based on the use of a hybrid approach that utilizes both a classical processor and a quantum processor as discussed herein. Further, the system 100 (and other embodiments discussed herein) provides a practical application related to simulating molecular systems that have sizes that were previously not able to be evaluated using only a classical processor. Previously, a purely classical iterative Density Matrix Renormalization Group-Density-Functional Theory (DMRG-DFT) embedding was utilized and such procedures exist for classical computing to embed a high-accuracy (and hence very expensive) method into a low-accuracy one, such as density-functional theory. Further, previously with the use of quantum processors, the core electrons were omitted through effective core potentials. Further, electrons were frozen and their excitations in the variational form was disregarded. Additionally, previous techniques could improve accuracy of active space embedding by leveraging quantum subspace expansions. However, the previous active space calculations are not accurate due to missing correlation from the frozen electrons. In addition, the freezing of electrons does not necessarily reduce the number of qubits. However, with the various embodiments discussed herein, massive qubit reduction can be achieved. Additionally, the active space can be embedded iteratively into a classical method (e.g., the classical processor). Accordingly, the disclosed aspects use density-functional theory to generate the subspace Hamiltonian used in the quantum calculation. In addition, the subsystem 'quantum' density is fed back into a density-functional theory and reoptimize the orbitals of the full system classically.

Further, the disclosed aspects are driven by new technology (e.g., quantum) to solve problems associated with providing only simulating molecular systems of a limited size. Additionally, the disclosed aspects can recover about one third of the error made by prior methods. The system 100 can also be fully operational towards performing one or more other functions (e.g., fully powered on, fully executed, etc.) while also performing the above-referenced computing processes.

Figure 2:
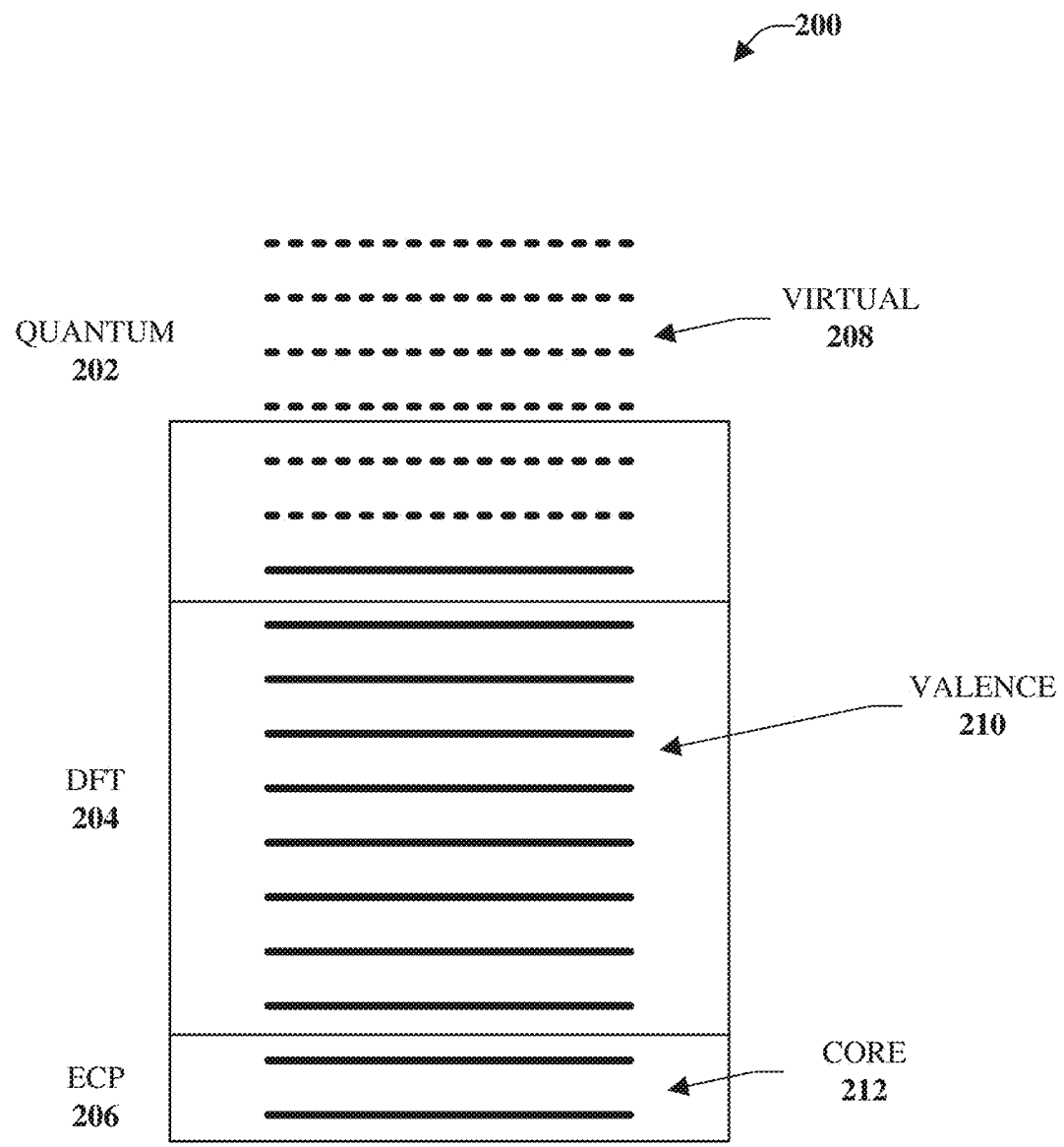
FIG. 2 illustrates example, non-limiting, notations for molecular orbitals and indicates their associated type in accordance with one or more embodiments described herein.

In further detail, FIG. 2 illustrates example, non-limiting, notations 200 for molecular orbitals and indicates their associated type in accordance with one or more embodiments described herein. Repetitive description of like elements employed in other embodiments described herein is omitted for sake of brevity.

The notation 200 includes notations for a quantum portion, a Density-Functional Theory or DFT 204 portion, and Effective Core Potentials or ECP portion 206. As discussed above, ECPs replace the core electrons in a calculation with an effective potential, thereby eliminating the need for core basis functions, which usually require a large set of Gaussians to describe the core basis functions. By means of active space embedding it is possible to freeze a subset of the molecular orbitals of a system; the remaining (unfrozen) set is referred to as the active space.

The annotations on the right ("virtual," "valence," and "core") indicate the respective orbitals. Virtual 208 refers to the orbitals represented by the dotted line, or dotted orbitals (the quantum portion 202). Valence 210 refers to the orbitals represented by the solid line or solid orbitals (the DFT 204). Core 212 refers to the orbitals represented by the solid lines or solid orbitals (the ECP portion 206).

The valence 210 can be treated quantum mechanically and correspond to the horizontal lines, where one horizontal line represents a single qubit. Accordingly, many qubits are needed in order to embed this space into a quantum computer. With the disclosed aspects, the quantum portion 202 can be reduced to a smaller subsection of orbitals. Thus, the valence 210 can represent the qubits that can be frozen. The valence 210 can be replaced with classical computing (e.g., the first computing processor 106) because a portion of the active electrons, the valence electrons, can be replaced with density-functional theory. Accordingly, the number of qubits necessary can be reduced dynamically, as indicated be the virtual 208, which represents the quantum processor (e.g., the second computing processor 112).

Figure 3:
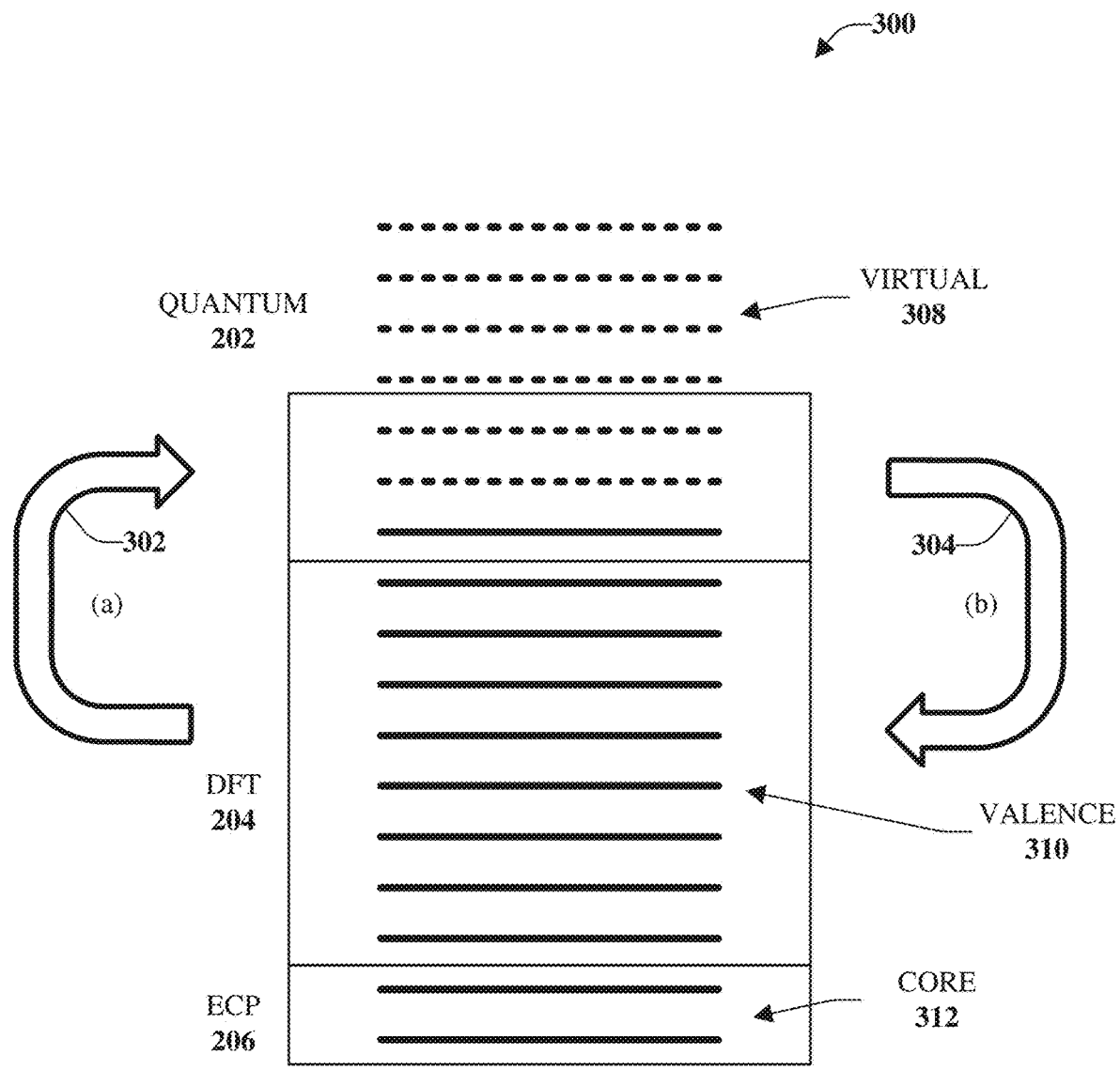
FIG. 3 illustrates an example, non-limiting, representation of molecular orbitals and indicates their associated type and the use of iterative density-functional theory-based embedding for a hybrid classical processor and quantum processor system in accordance with one or more embodiments described herein.

FIG. 3 illustrates an example, non-limiting, representation of molecular orbitals and indicates their associated type and the use of iterative density-functional theory-based embedding for a hybrid classical processor and quantum processor system in accordance with one or more embodiments described herein. Repetitive description of like elements employed in other embodiments described herein is omitted for sake of brevity.

A determination utilizing density-functional theory (DFT 204) can be performed in the frozen portion of the quantum processor (e.g., the valence 210). The DFT 204 can be performed using a classical computing processor (e.g., the first computing processor 106). The results of the DFT 204 can be passed to the unfrozen portion of the quantum processor (e.g., the second computing processor 112), as indicated by the first arrow 302. The first arrow 302 represents the result of density-functional theory determination. Upon or after the result of the density-functional theory is passed to the quantum processor, processing using a Variational Quantum Eigensolver (VQE) can be performed. The results can be returned to the classical computing processor for further processing, as indicated by the second arrow 304.

In further detail, for active space embedding, the frozen electrons can be treated outside of the quantum hardware by using a classical method such as density-functional theory. The energy (E) becomes:

$$E = E^I + E^A = \frac{1}{2}\sum_{ij}(h_{ij} + F_{ij}^I)D_{ij}^I + \sum_{uv}F_{uv}^I D_{uv}^A + \frac{1}{2}\sum_{uvxy}g_{uvxy}d_{uvxy}^A. \quad \text{Equation 1}$$

where E is electronic energy, D is 1-electron density matrix, d is 2-electron density matrix, F is the Fock operator matrix, h is 1-electron integrals, and g is 2-electron integrals. Further, superscript I indicates inactivity, superscript A indicates activity, subscripts i, j, k, l, m, and n indicate inactive indices, subscripts u, v, x, and y indicate active indices, subscripts a, b, c, and d indicate virtual indices, and subscripts p, q, r, and s indicate general (e.g., any) indices. In addition, the inactive Fock operator $F^I$ adds the effective potential of the inactive (frozen) electrons on to the 1-electron integrals:

$$F_{mn}^I + h_{mn} + \sum_{i}^{inact.} 2g_{iimn} - g_{inmi}. \quad \text{Equation 2}$$

For range separation, the Coulomb operator can be split into a long-range and short-range part:

$$\frac{1}{r_{12}} = \frac{\text{erf}(\mu r_{12})}{r_{12}} + \frac{1 - \text{erf}(\mu r_{12})}{r_{12}}. \quad \text{Equation 3}$$

where $r_{12}$ is the distance between two general electrons 1 and 2, erf is the error function, μ is a range-separation parameter of unit a.u.$^{(-1)}$ rendering the argument of the error function unitless, and where a.u. is an atomic unit.

Figure 4:
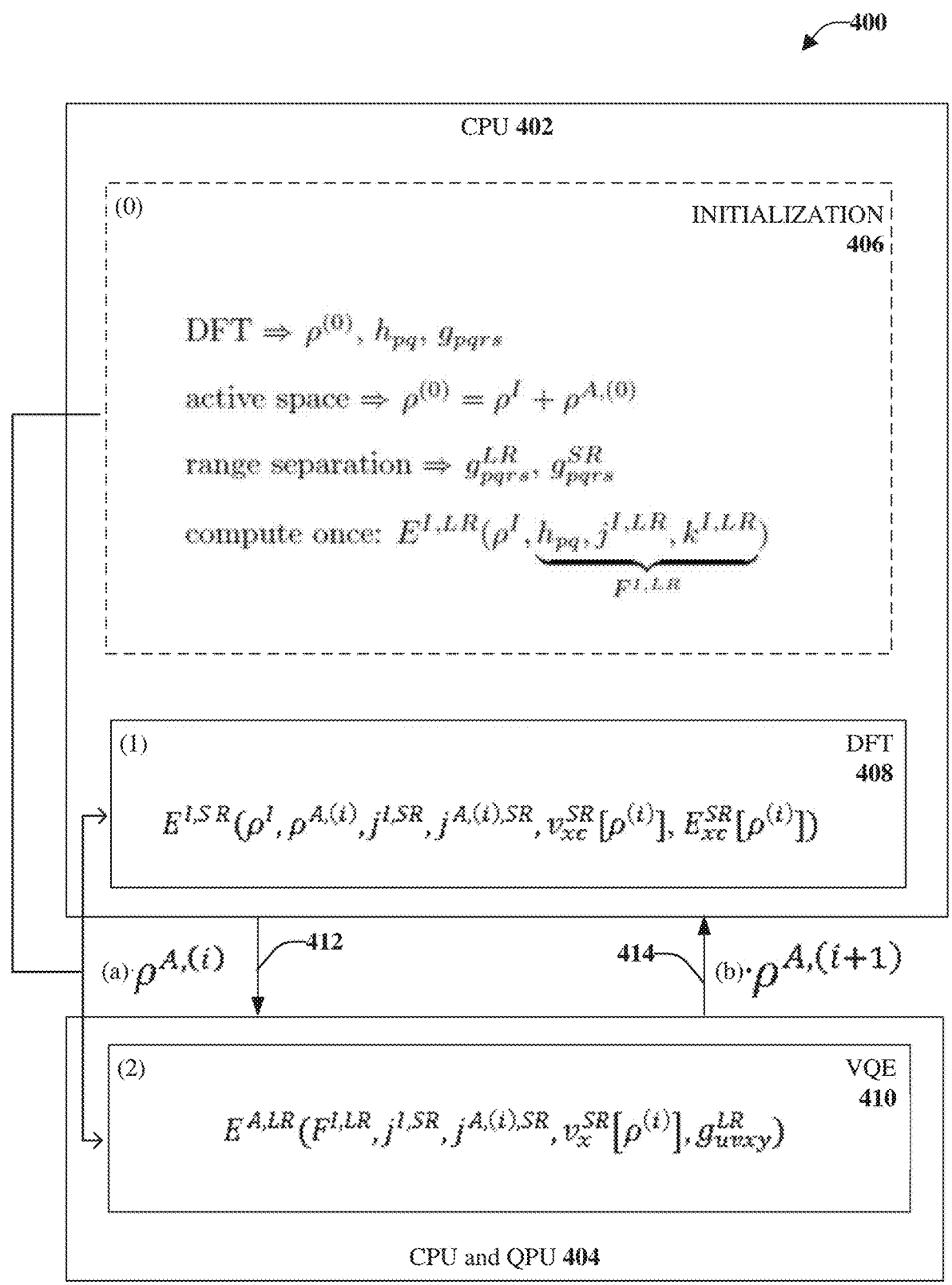
FIG. 4 illustrates an example, non-limiting system that comprises an iterative hybrid quantum and classical protocol in accordance with one or more embodiments described herein.

FIG. 4 illustrates an example, non-limiting system 400 that comprises an iterative hybrid quantum and classical protocol in accordance with one or more embodiments described herein. Repetitive description of like elements employed in other embodiments described herein is omitted for sake of brevity.

Illustrated are a CPU portion 402 (e.g., the first computing processor 106) and a CPU and QPU portion 404 (e.g., the second computing processor 112). Initialization 406 can be performed at the CPU portion 402. For example, initialization can be performed on the classical computer using a using a Kohn-Sham density-functional theory (DFT) calculation, such as, for example:

$$DFT \Rightarrow \rho^{(0)}, h_{pq}, g_{pqrs} \quad \text{Equation 4.}$$

where ρ is electron density and superscript (i) is the i-th iterative step (where i equals 0 for the initialization).

For example, the density can be split into an active space as follows:

$$\text{active space} \Rightarrow \rho^{(i)} = \rho^{(0)} + \rho^{A,(0)} \quad \text{Equation 5.}$$

Further, electron-repulsion integrals can be separated by range.

$$\text{range separation} \Rightarrow g_{pqrs}^{LR}, g_{pqrs}^{SR} \quad \text{Equation 6.}$$

where superscript LR is "long range" and superscript SR is "short range."

The inactive long-range energy can be computed once:

$$\text{compute once:} \Rightarrow E^{I,LR}\left(\rho^I, h_{pq}, \underbrace{j^{I,LR}, K^{I,LR}}_{F^{I,LR}}\right). \quad \text{Equation 7}$$

where j is the 2-electron Coulomb matrix and K is the 2-electron exchange matrix.

Further, in the CPU portion 402, a density-functional theory 408 can be calculated. For example, inactive short-range contributions can be determined. Such determination can be made based on:

$$E^{I,SR}(\rho^I, \rho^{A,(i)} j^{I,SR}, j^{A,(i),SR}, v_{xc}^{SR}[\rho^{(i)}], E_{xc}^{SR}[\rho^{(i)}]) \quad \text{Equation 8.}$$

where subscript "xc" is the exchange-correlation, where $\rho^{A,(i)}$ is the active density matrix, which can be passed to the CPU and QPU portion 404, as indicated at 412. In the CPU and QPU portion 404, VQE 410 can be performed where long-range contributions can be determined. Further, the active density matrix can be updated:

$$E^{A,LR}(F^{I,LR}, j^{I,SR}, j^{A,(i),SR}, v_x^{SR}[\rho^{(i)}], g_{uvxy}^{LR}) \qquad \text{Equation 9.}$$

The new density $\rho^{A,(i+1)}$ can be returned to the density-functional theory 408, as indicated at 414, for further processing.

On classical computers, the various aspects provided herein related to improving density-functional theory calculations is not possible. Further, the type of calculations provided herein using the embedding scheme classically will have unfavorable scaling and, therefore, the size of a molecular system able to be analyzed is limited. Accordingly, the exact classical calculations can be extracted to a quantum system that is smaller, and that can be achieved with near-term quantum computers. Quantum computers can take all degrees of freedom and perform the processing with favorable scaling. In the near-term with the disclosed aspects, it is possible to reduce the number of electrons to a minimum set of orbitals. The orbitals that live in the active space, so that the disclosed aspects can be implemented in the near term with quantum computers.

As discussed, quantum algorithms can be coupled to density-functional theory simulations through iterative procedures. This also enables the initialization quantum computations with density-functional theory instead of HF orbitals previously performed. Additionally, based on the advancements of quantum processors, many other advanced classical methods can also be coupled to density-functional theory simulations. Accordingly, molecular systems of increasingly larger sizes can be simulated. The upper limit can be defined by which ever system can be treated on a classical computer using the low-level approximation method.

Figure 5:
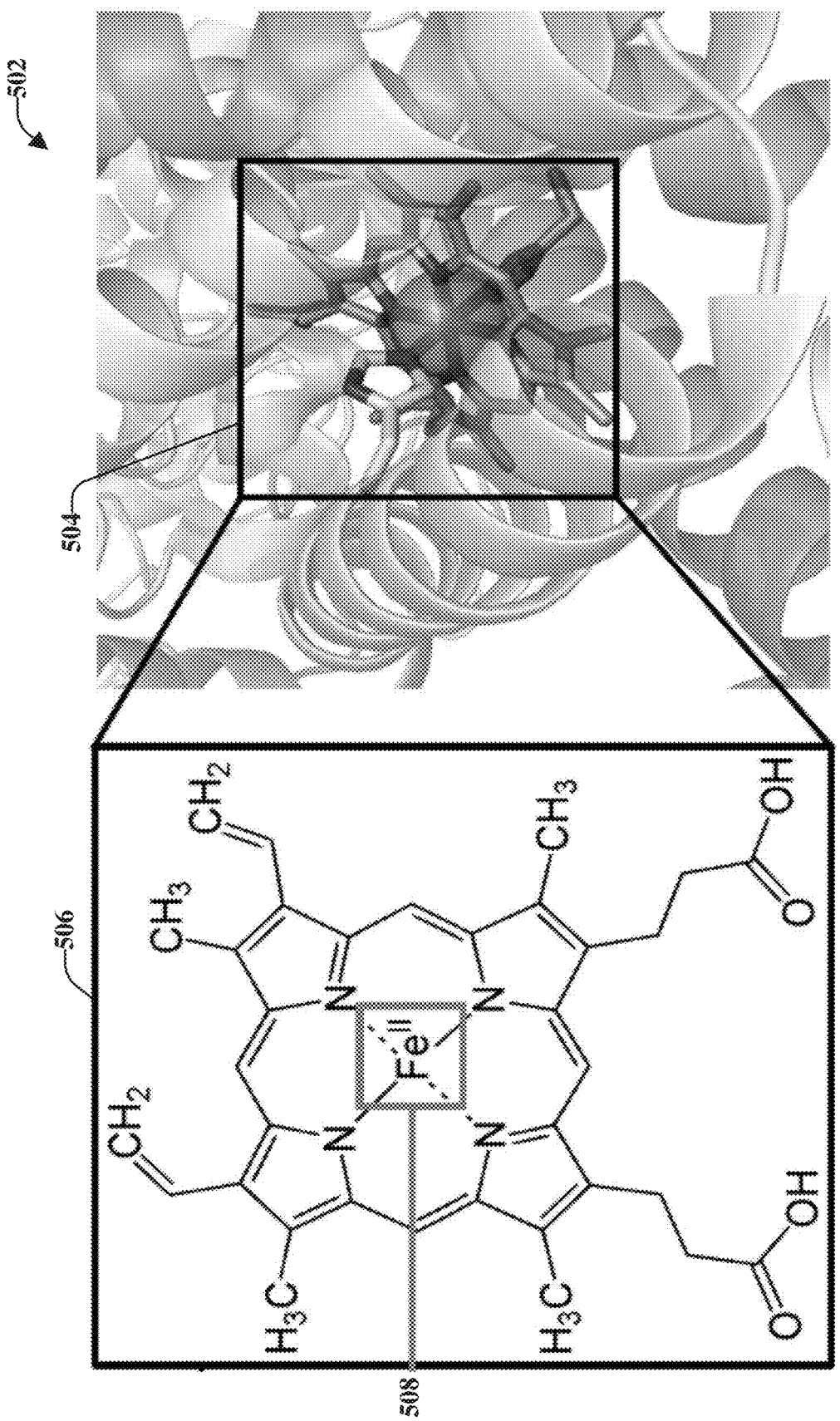
FIG. 5 illustrates an example, non-limiting, representation of a molecule of interest, which becomes treatable with the disclosed embedding procedure in accordance with one or more embodiments described herein.

FIG. 5 illustrates an example, non-limiting, representation of a molecule of interest, which becomes treatable with the disclosed embedding procedure in accordance with one or more embodiments described herein. Repetitive description of like elements employed in other embodiments described herein is omitted for sake of brevity.

As mentioned, the disclosed aspects can treat molecular systems as large as (if not larger than) those molecular systems that can be handled on classical hardware. For example, treating the iron metal inside the Fe-porphyrin-like structure Heme. Heme is a coordination complex that includes an iron ion coordinated to a porphyrin acting as a tetradentate ligand, and to one or two axial ligands.

On the right of FIG. 5 is a representation 502 of the Heme group of succinate dehydrogenase, an electron carrier in the mitochondrial electron transfer chain, is bound to two histidines. The large semi-transparent sphere indicates the location of the iron ion. The porphyrin moiety in box 504 is shown with atomistic detail in the enlargement 506, which is a structure of Fe-porphyrin subunit of Heme B.

The molecular structure depicted in the enlargement 506 is an example of what can become visible by implementing the disclosed aspects. The disclosed aspects can treat the boxed portion 508 (e.g., the iron atom) using the quantum processor as discussed herein. This is an ion core embedded in a protein. The other atoms in the environment of the molecular structure depicted in the enlargement 506 can be treated as the density-functional theory by the classical processor. Further, the molecular structure can be surrounded by other atoms, as indicated by the representation 502 on the right of FIG. 5, which can also be treated as discussed herein.

FIGS. 6A-6D illustrate plots of different results obtained for a pyridine molecule in accordance with one or more embodiments described herein. Repetitive description of like elements employed in other embodiments described herein is omitted for sake of brevity.

The pyridine molecule comprises the following structure:

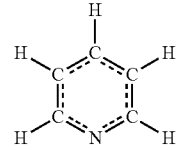

Figure 6A:
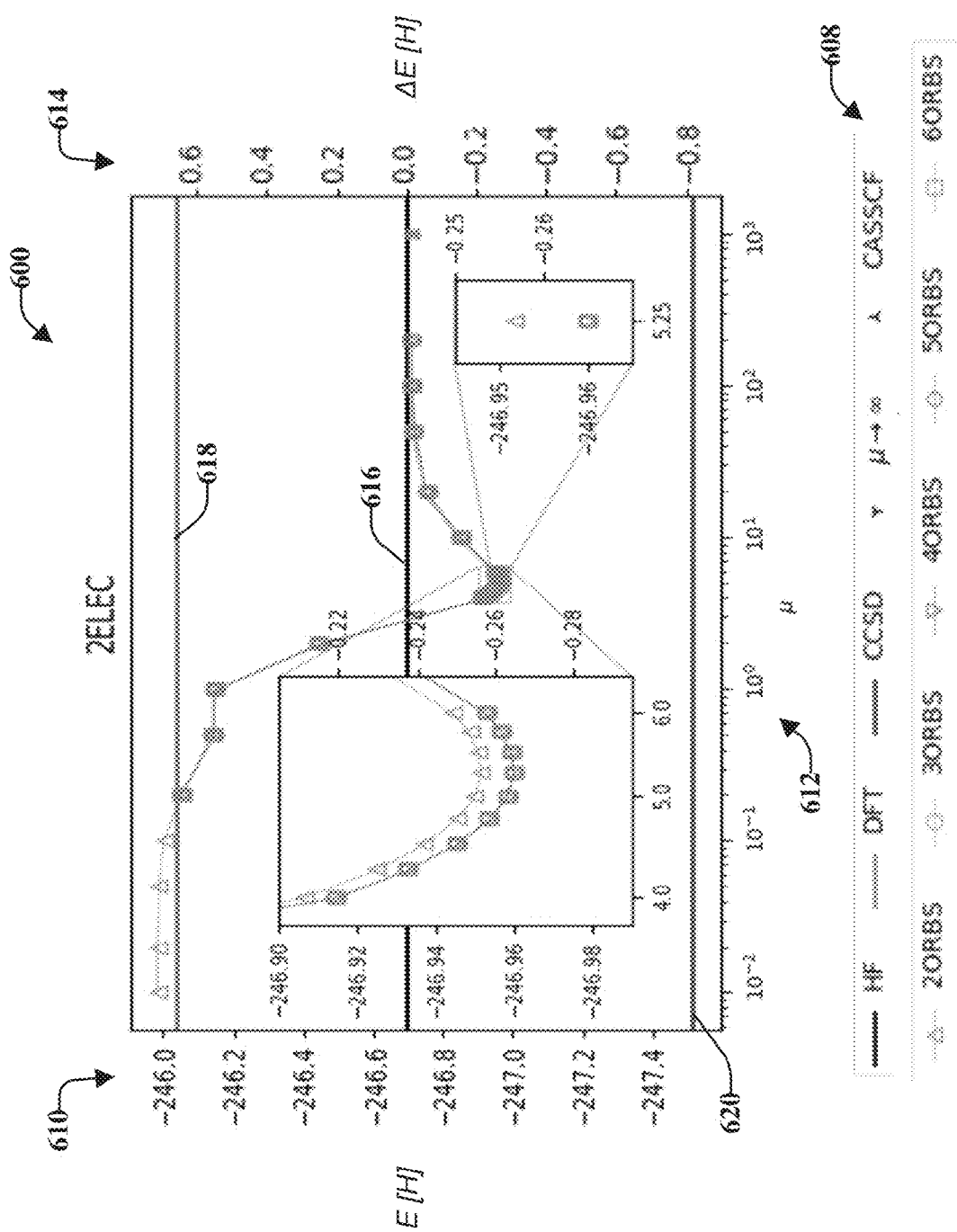
FIGS. 6A-6D illustrate plots of different results obtained for a pyridine molecule in accordance with one or more embodiments described herein.
Figure 6B:
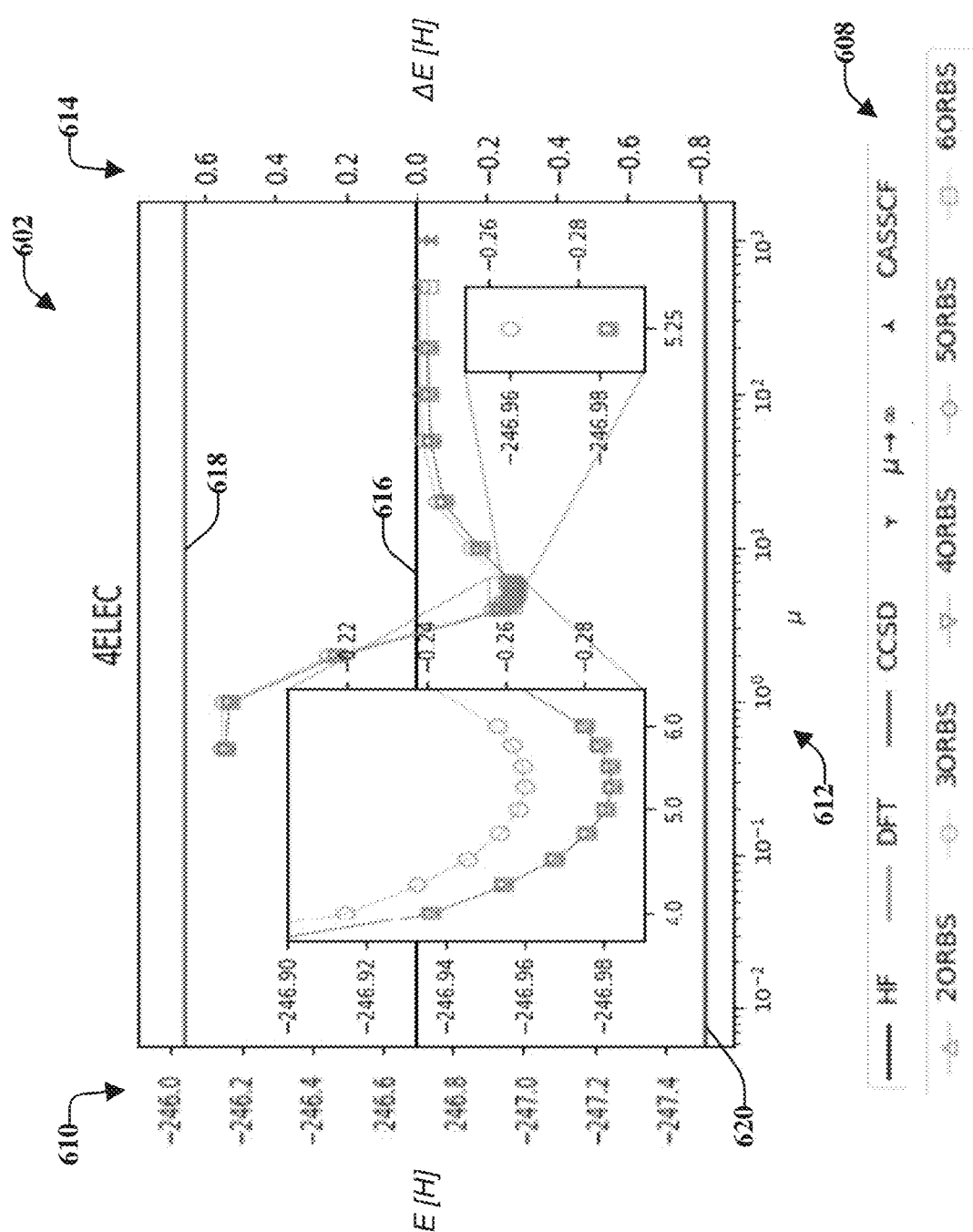
Figure 6C:
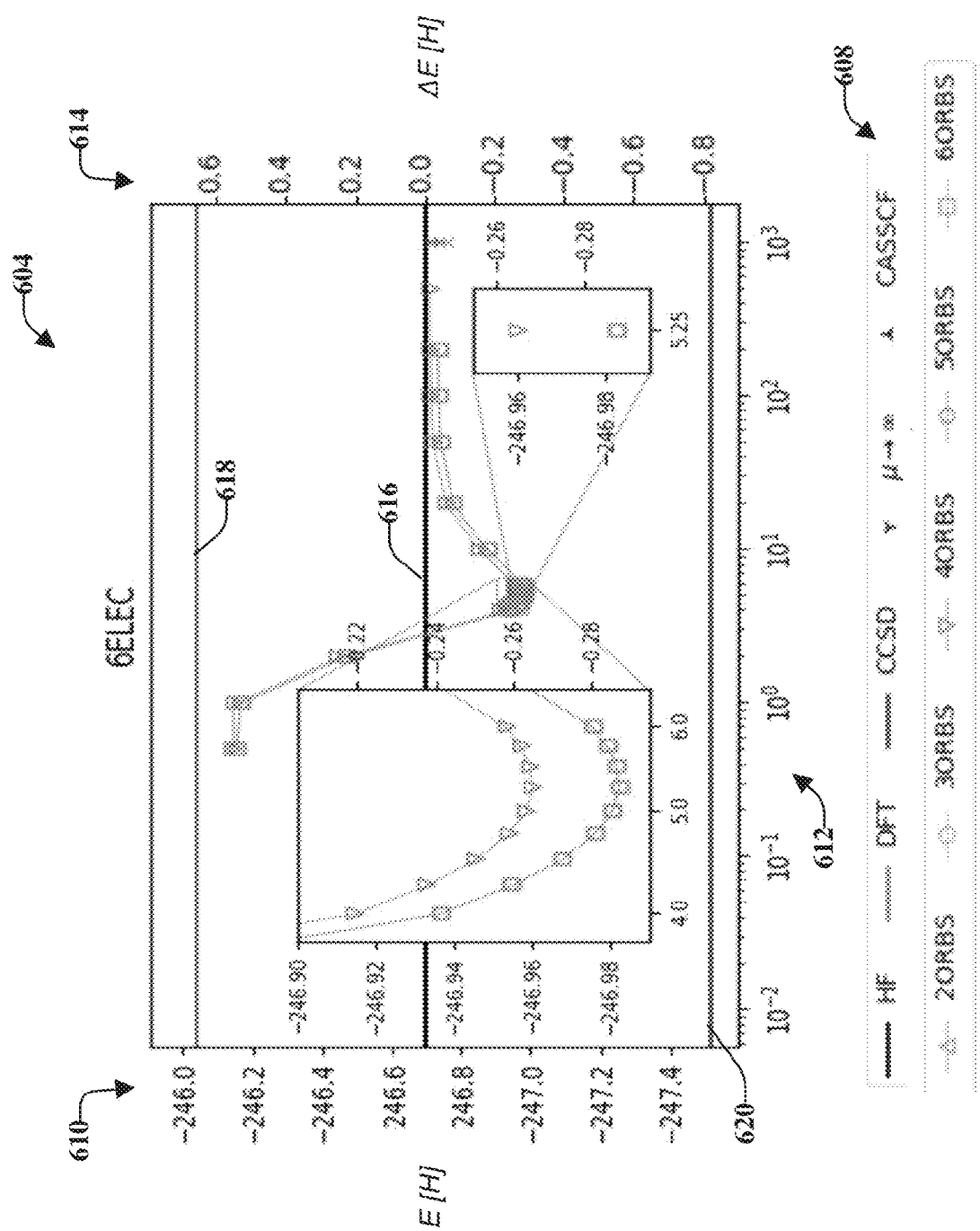
Figure 6D:
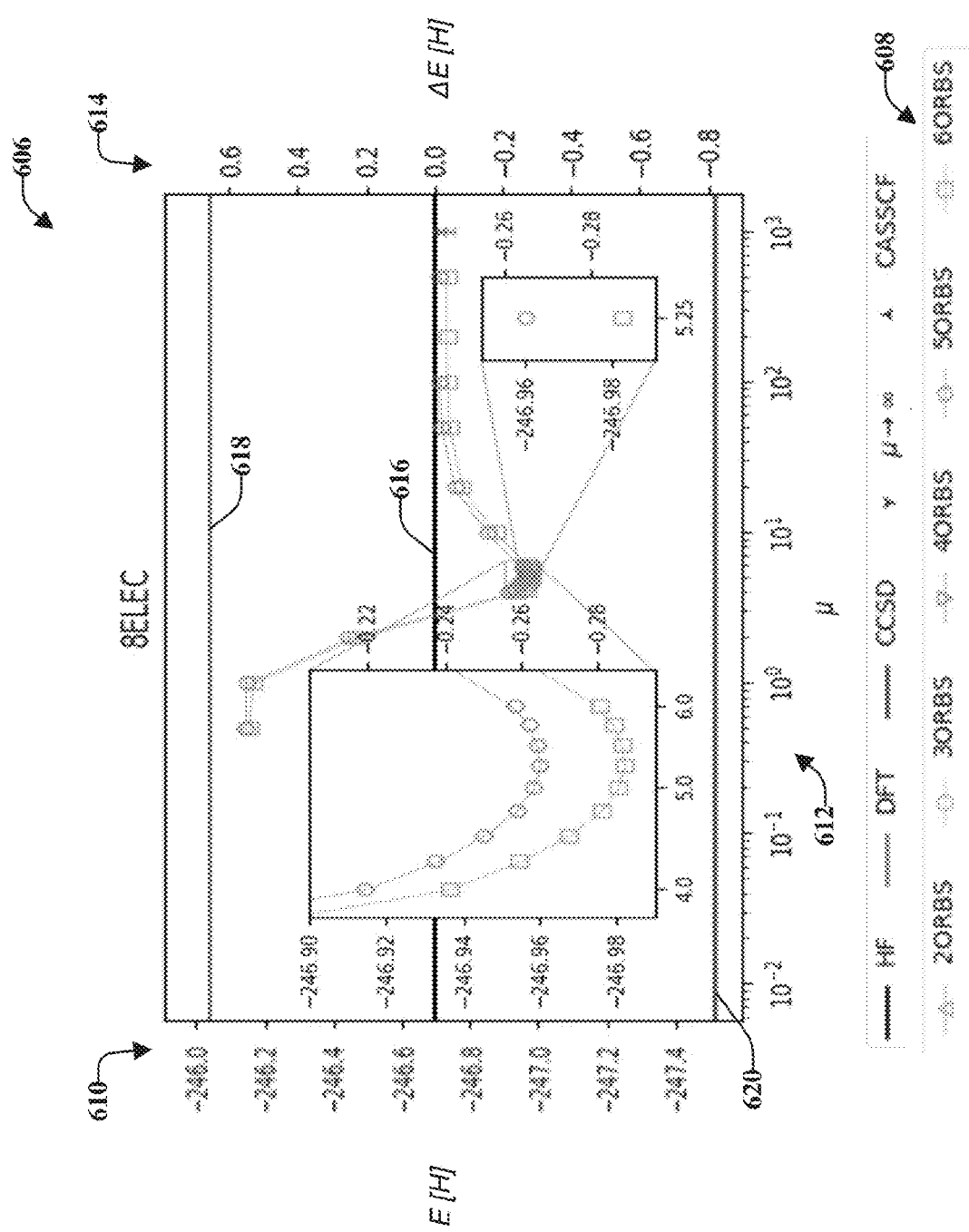

The results of FIGS. 6A-6D demonstrate how much energy can be captured utilizing the disclosed aspects. FIG. 6A illustrates a first plot 600 for two active electrons; FIG. 6B illustrates a second plot 602 for four active electrons; FIG. 6C illustrates a third plot 604 for six active electrons; and FIG. 6D illustrates a fourth plot 606 for eight active electrons. A legend 608 is illustrated below the respective plots.

Energy in Hartee (E[H]) is illustrated on the left vertical axis 610. Range-separation parameter μ is illustrated on the horizontal axis 612. The change in Energy (ΔE[H]) is illustrated on the right vertical axis 614. Accordingly, the plots illustrate E[H] against range-separation parameter μ. Further, the results are group by active spaces.

HF orbitals are represented by line(s) 616; density-functional theory is represented by line(s) 618; and Coupled Cluster Single Double (CCSD) is represented by line(s) 620. Line symbols indicate the number of active molecular orbitals. Two orbitals is indicated by line(s) with right-side up triangles; three orbitals is indicated by line(s) with circles; four orbitals is indicated by line(s) with upside down triangles; five orbitals is indicated by line(s) with circles; and six orbitals is indicated by line(s) with squares.

The initial calculation for the plot is RHF (relative energies on right y-axis). Symbol μ approaching zero (μ→0) indicates that energy converges towards density-functional theory (XC: lda,vwn). Symbol μ approaching infinity (μ→∞) indicates converging to non-iterative embedding (bound by Complete Active Space Self-Consistent Field (CASSCF) with same active space). Further, CCSD (Coupled Cluster calculations with all Single and Double excitations) energy as almost exact reference.

As demonstrated by the plots of FIGS. 6A through 6D, the disclosed aspects can be applied to achieve desired results. Further, the disclosed aspects can be applied to simulate systems of increasing larger sizes. The upper limit can be defined by which ever system can be treated on a classical computer using a low-level approximation method.

Further, the long term impact of the disclosed aspects is that systems can be simulated with a modest number of qubits because the calculations can be focused on the portion of the system that is difficult to implement or treat classically (e.g., via a classical processor). Additionally, the overall computing system or device can be smaller because of embedding the classical processor with the quantum processor. Further, not everything is needed to be taken to the quantum level, instead the difficult parts can be implemented by a quantum processor and the other, less difficult, parts can be implemented by a classical processor.

Figure 7:
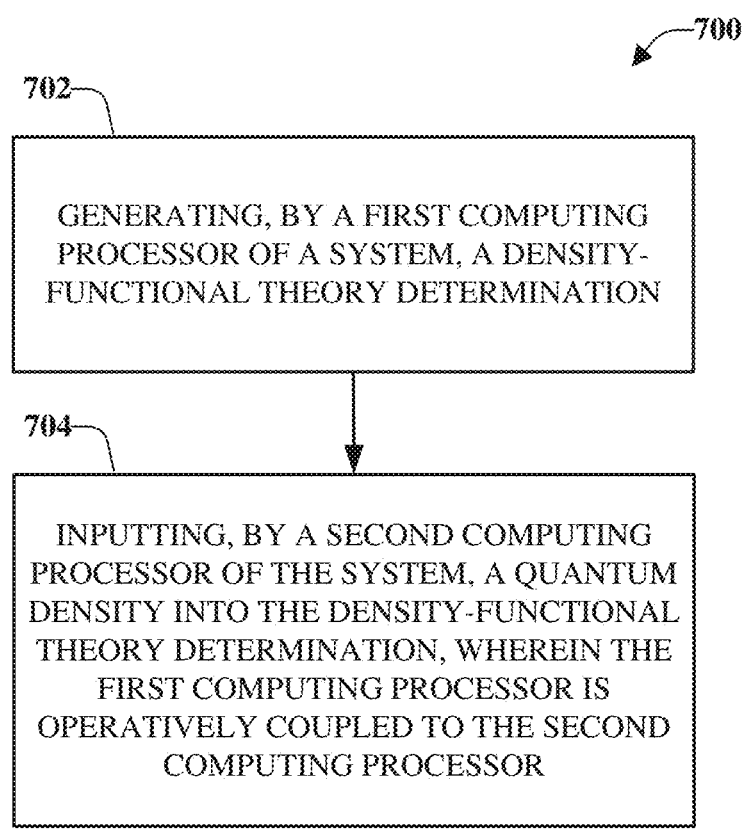
FIG. 7 illustrates a flow diagram of an example, non-limiting, computer-implemented method that facilitates density-functional theory determinations using a quantum computing system in accordance with one or more embodiments described herein.

FIG. 7 illustrates a flow diagram of an example, non-limiting, computer-implemented method 700 that facilitates density-functional theory determinations using a quantum computing system in accordance with one or more embodiments described herein. Repetitive description of like elements employed in other embodiments described herein is omitted for sake of brevity.

At 702 of the computer-implemented method 700, a first computing processor of a system can generate density-functional theory determination (e.g., via the first computing processor 106). The density-function theory determination can be an active density matrix, according to some implementations. Further, at 704 of the computer-implemented method 700, a second computing processor of the system can input a quantum density into the density-functional theory determination (e.g., via the second computing processor 112). The first computing processor can be operatively coupled to the second computing processor. In an example, the second computing processor can be a quantum computing processor and the first computing processor can be a classical computing processor.

Figure 8:
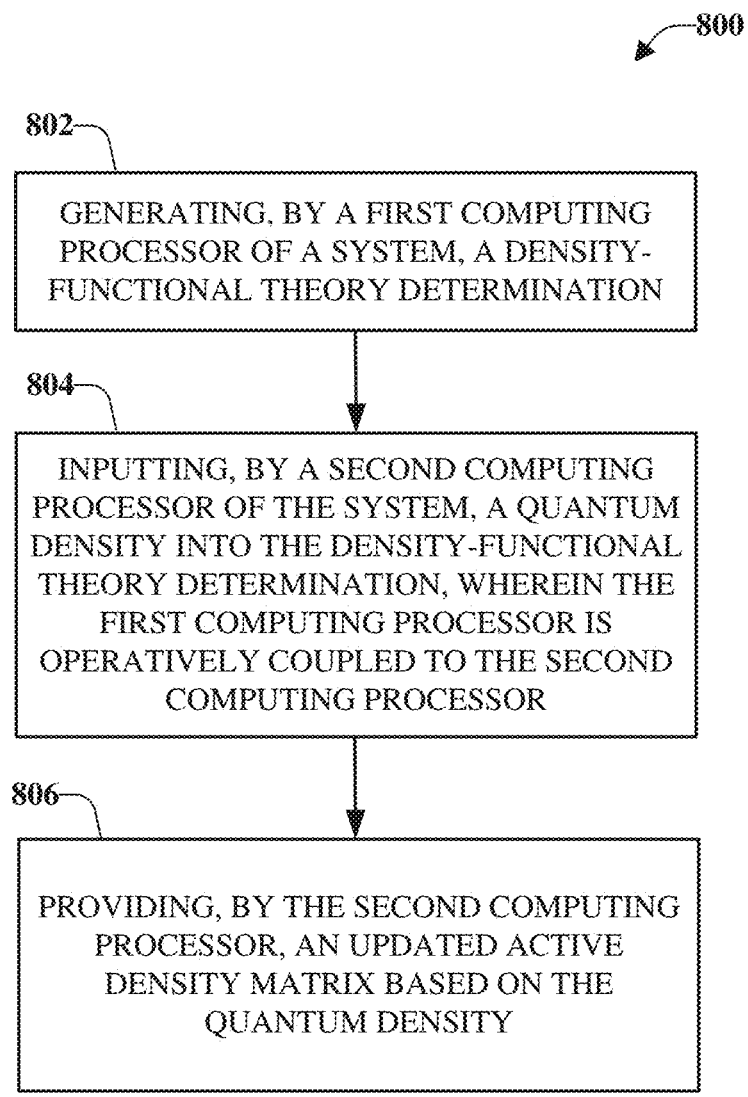
FIG. 8 illustrates a flow diagram of an example, non-limiting, computer-implemented method that facilitates mitigating a quantity of qubits utilized for performing density-functional theory determinations using a quantum computing system in accordance with one or more embodiments described herein.

FIG. 8 illustrates a flow diagram of an example, non-limiting, computer-implemented method 800 that facilitates mitigating a quantity of qubits utilized for performing density-functional theory determinations using a quantum computing system in accordance with one or more embodiments described herein. Repetitive description of like elements employed in other embodiments described herein is omitted for sake of brevity.

At 802 of the computer-implemented method 800, a first computing processor of a system generates a density-functional theory determination (e.g., via the first computing processor 106). The density-functional theory determination can be an active density matrix. According to some implementations, the first computing processor can determine inactive short-range contributions resulting in the density-functional theory determination.

At 804 of the computer-implemented method 800, a second computing processor of the system inputs a quantum density into the density-functional theory determination (e.g., via the second computing processor 112). The first computing processor and the second computing processor are operatively coupled. For example, by operatively coupling the first computing processor and the second computing processor a number of qubits utilized by the second computing processor to update the active density matrix can be mitigated.

Further, at 806 of the of the computer-implemented method 800, the second computing processor provides an updated active density matrix based on the quantum density (e.g., via the second computing processor 112 or a feedback component (not shown)). For example, the updated active density matrix can be provided or fed back to the first computing processor. Accordingly, the second computing processor can communicate the updated active density matrix to the first computing processor. The communicating is performed iteratively according to some implementations.

Figure 9:
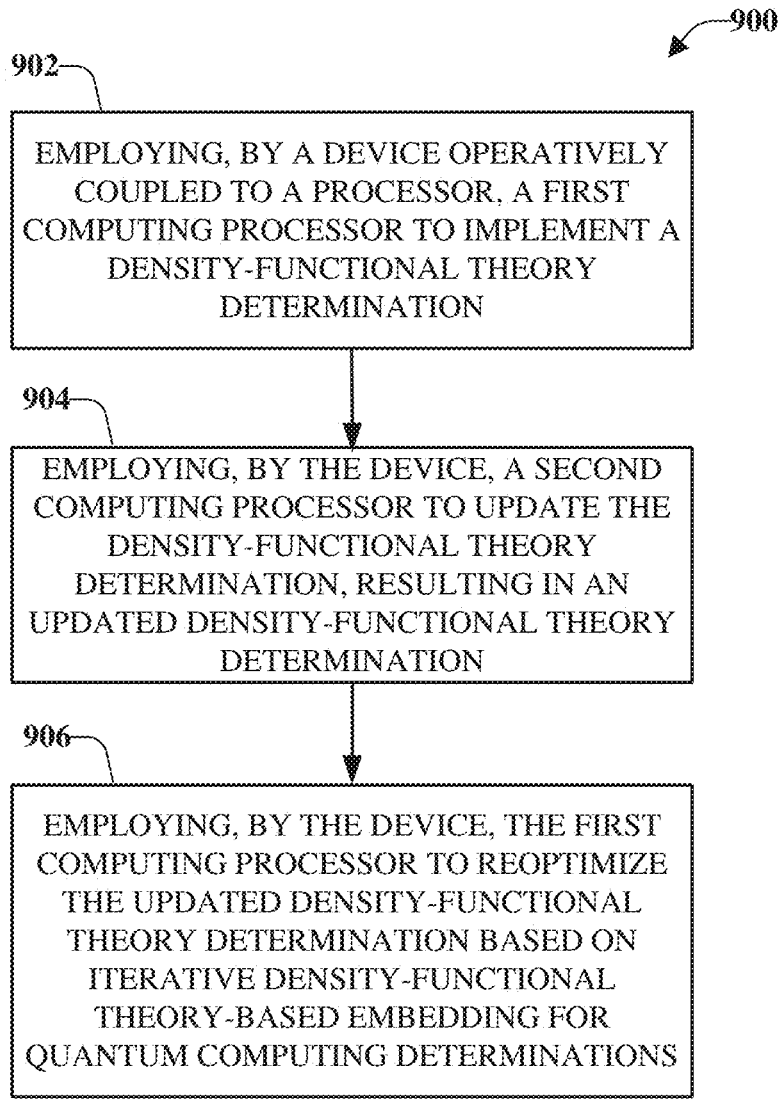
FIG. 9 illustrates a flow diagram of an example, non-limiting, computer-implemented method that facilitates a feedback loop related to density-functional theory determinations using a quantum computing system in accordance with one or more embodiments described herein.

FIG. 9 illustrates a flow diagram of an example, non-limiting, computer-implemented method 900 that facilitates a feedback loop related to density-functional theory determinations using a quantum computing system in accordance with one or more embodiments described herein. Repetitive description of like elements employed in other embodiments described herein is omitted for sake of brevity.

At 902 of the computer-implemented method 900, a device operatively coupled to a processor can employ a first computing processor to implement a density-functional theory determination (e.g., via the first computing processor 106, or a coupling component (not shown)). Further, at 904 of the computer-implemented method 900, the device can employ a second computing processor to update the density-functional theory determination, resulting in an updated density-functional theory determination (e.g., via the second computing processor 112). According to some implementations, the first computing processor can comprise a classic processor, and the second computing processor can comprise a quantum processor.

Upon or after the updated density-functional theory determination is determined by the second computing processor, at 906 of the computer-implemented method 900, the device can employ the first computing processor to reoptimize the updated density-functional theory determination based on iterative density-functional theory-based embedding for quantum computing determinations (e.g., via the first computing processor 106 or a feedback component). Employing the first computing processor can comprise avoiding frozen electrons in the second computing processor.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 10:
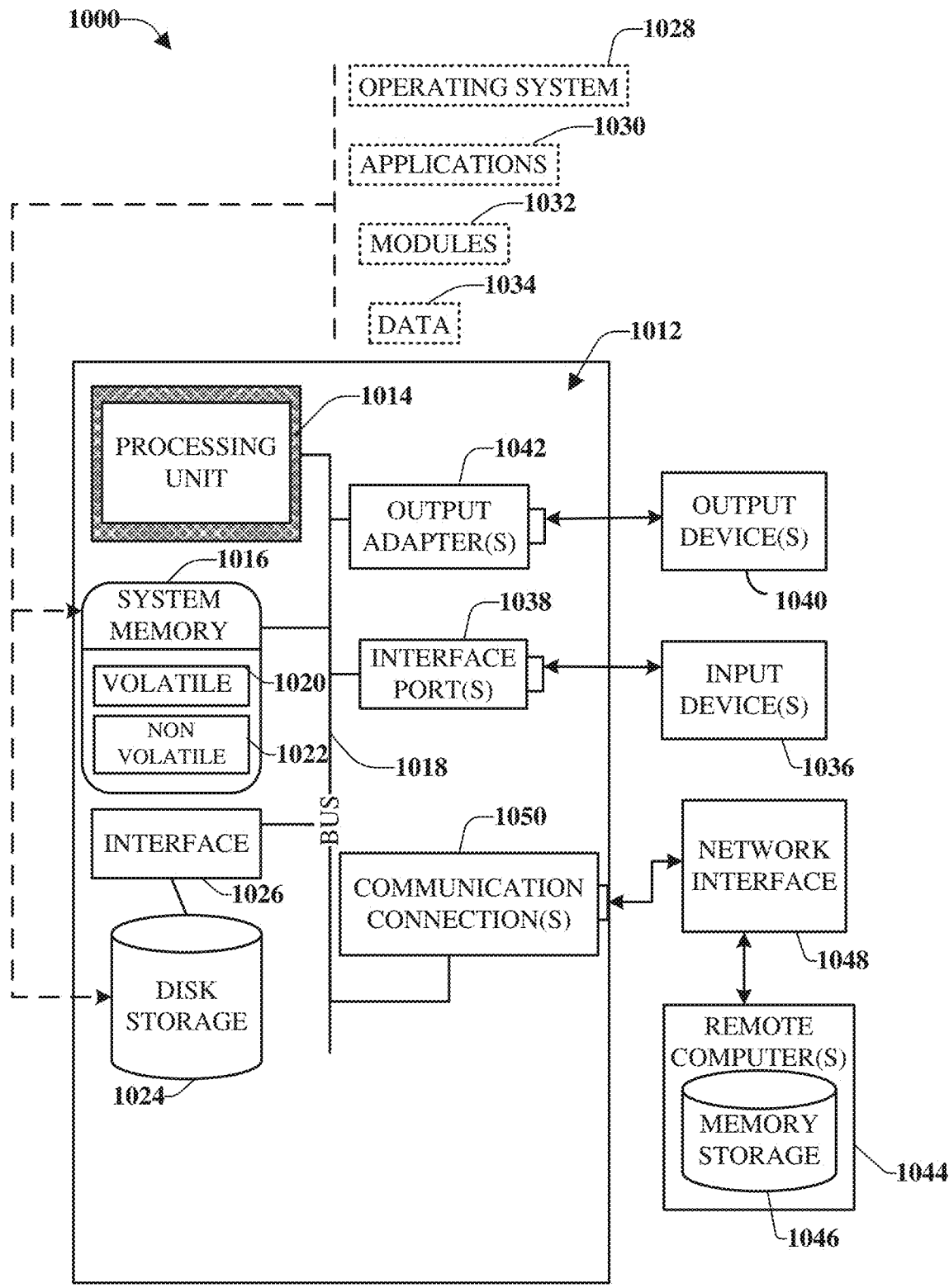
FIG. 10 illustrates a block diagram of an example, non-limiting operating environment in which one or more embodiments described herein can be facilitated.

In order to provide a context for the various aspects of the disclosed subject matter, FIG. 10 as well as the following discussion are intended to provide a general description of a suitable environment in which the various aspects of the disclosed subject matter can be implemented. FIG. 10 illustrates a block diagram of an example, non-limiting operating environment in which one or more embodiments described herein can be facilitated. Repetitive description of like elements employed in other embodiments described herein is omitted for sake of brevity. With reference to FIG. 10, a suitable operating environment 1000 for implementing various aspects of this disclosure can also include a computer 1012. The computer 1012 can also include a processing unit 1014, a system memory 1016, and a system bus 1018. The system bus 1018 couples system components including, but not limited to, the system memory 1016 to the processing unit 1014. The processing unit 1014 can be any of various available processors. Dual microprocessors and other multiprocessor architectures also can be employed as the processing unit 1014. The system bus 1018 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI). The system memory 1016 can also include volatile memory 1020 and nonvolatile memory 1022. The basic input/output system (BIOS), containing the basic routines to transfer information between elements within the computer 1012, such as during start-up, is stored in nonvolatile memory 1022. By way of illustration, and not limitation, nonvolatile memory 1022 can include read only memory (ROM), programmable ROM (PROM), electrically programmable ROM (EPROM), electrically erasable programmable ROM (EEPROM), flash memory, or nonvolatile random access memory (RAM) (e.g., ferroelectric RAM (FeRAM)). Volatile memory 1020 can also include random access memory (RAM), which acts as external cache memory. By way of illustration and not limitation, RAM is available in many forms such as static RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM.

Computer 1012 can also include removable/non-removable, volatile/non-volatile computer storage media. FIG. 10 illustrates, for example, a disk storage 1024. Disk storage 1024 can also include, but is not limited to, devices like a magnetic disk drive, floppy disk drive, tape drive, Jaz drive, Zip drive, LS-100 drive, flash memory card, or memory stick. The disk storage 1024 also can include storage media separately or in combination with other storage media including, but not limited to, an optical disk drive such as a compact disk ROM device (CD-ROM), CD recordable drive (CD-R Drive), CD rewritable drive (CD-RW Drive) or a digital versatile disk ROM drive (DVD-ROM). To facilitate connection of the disk storage 1024 to the system bus 1018, a removable or non-removable interface is typically used, such as interface 1026. FIG. 10 also depicts software that acts as an intermediary between users and the basic computer resources described in the suitable operating environment 1000. Such software can also include, for example, an operating system 1028. Operating system 1028, which can be stored on disk storage 1024, acts to control and allocate resources of the computer 1012. System applications 1030 take advantage of the management of resources by operating system 1028 through program modules 1032 and program data 1034, e.g., stored either in system memory 1016 or on disk storage 1024. It is to be appreciated that this disclosure can be implemented with various operating systems or combinations of operating systems. A user enters commands or information into the computer 1012 through input device(s) 1036. Input devices 1036 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1014 through the system bus 1018 via interface port(s) 1038. Interface port(s) 1038 include, for example, a serial port, a parallel port, a game port, and a universal serial bus (USB). Output device(s) 1040 use some of the same type of ports as input device(s) 1036. Thus, for example, a USB port can be used to provide input to computer 1012, and to output information from computer 1012 to an output device 1040. Output adapter 1042 is provided to illustrate that there are some output devices 1040 like monitors, speakers, and printers, among other output devices 1040, which require special adapters. The output adapters 1042 include, by way of illustration and not limitation, video and sound cards that provide a method of connection between the output device 1040 and the system bus 1018. It should be noted that other devices and/or systems of devices provide both input and output capabilities such as remote computer(s) 1044.

Computer 1012 can operate in a networked environment using logical connections to one or more remote computers, such as remote computer(s) 1044. The remote computer(s) 1044 can be a computer, a server, a router, a network PC, a workstation, a microprocessor based appliance, a peer device or other common network node and the like, and typically can also include many or all of the elements described relative to computer 1012. For purposes of brevity, only a memory storage device 1046 is illustrated with remote computer(s) 1044. Remote computer(s) 1044 is logically connected to computer 1012 through a network interface 1048 and then physically connected via communication connection 1050. Network interface 1048 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1050 refers to the hardware/software employed to connect the network interface 1048 to the system bus 1018. While communication connection 1050 is shown for illustrative clarity inside computer 1012, it can also be external to computer 1012. The hardware/software for connection to the network interface 1048 can also include, for exemplary purposes only, internal and external technologies such as, modems including regular telephone grade modems, cable modems and DSL modems, ISDN adapters, and Ethernet cards.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create method for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments where tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other method to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or non-volatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim. The descriptions of the various embodiments have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A circuit, comprising:
a classical computing processor that generates a density-functional theory determination based on input data associated with a molecular system, comprising:
determining inactive long-range contributions of frozen electrons of the molecular system to the density-functional theory determination, and
determining inactive short-range contributions of the frozen electrons to the density-functional theory determination; and
a quantum computing processor that updates the density-functional theory determination by inputting a quantum density into the density-functional theory determination generated by the classical computing processor, wherein the quantum density is based on long-range contributions of unfrozen electrons of the molecular system, and wherein the classical computing processor is operatively coupled to the quantum computing processor.

2. The circuit of claim 1, wherein the classical computing processor separates electrons in the molecular system into the frozen electrons and the unfrozen electrons.

3. The circuit of claim 1, wherein the density-functional theory determination comprises an active density matrix, and wherein the quantum computing processor generates an updated active density matrix based on the quantum density.

4. The circuit of claim 1, wherein the quantum computing processor communicates the updated density-functional theory determination to the classical computing processor to perform an optimization of the updated density-functional theory determination.

5. The circuit of claim 4, wherein the optimization of the updated density-functional theory determination optimizes orbitals of electrons of the molecular system.

6. The circuit of claim 1, wherein the quantum computing processor employs a variational quantum eigensolver.

7. The circuit of claim 1, wherein the classical computing processor separates electron-repulsion integrals associated with electrons in the molecular system into a short-range and a long-range.

8. The circuit of claim 1, wherein the density-functional theory determination generated by the classical computing processor provides a subspace Hamiltonian used by the quantum computing processor.

9. A computer-implemented method, comprising:
  generating, by a classical computing processor of a system, a density-functional theory determination based on input data associated with a molecular system, comprising:
    determining inactive long-range contributions of frozen electrons of the molecular system to the density-functional theory determination, and
    determining inactive short-range contributions of the frozen electrons to the density-functional theory determination; and
  updating, by a quantum computing processor of the system, the density-functional theory determination by inputting a quantum density into the density-functional theory determination, wherein the quantum density is based on long-range contributions of unfrozen electrons of the molecular system, and wherein the classical computing processor is operatively coupled to the quantum computing processor.

10. The computer-implemented method of claim 9, wherein the classical computing processor separates electrons in the molecular system into the frozen electrons and the unfrozen electrons.

11. The computer-implemented method of claim 9, wherein the density-functional theory determination comprises an active density matrix, and wherein the computer-implemented method further comprises:
  providing, by the quantum computing processor, an updated active density matrix based on the quantum density.

12. The computer-implemented method of claim 11, further comprising:
  mitigating a number of qubits utilized by the quantum computing processor to update the active density matrix based on the classical computing processor being operatively coupled to the quantum computing processor.

13. The computer-implemented method of claim 9, further comprising:
  communicating, by the quantum computing processor, the updated density-functional theory determination to the classical computing processor to perform an optimization of the updated density-functional theory determination.

14. The computer-implemented method of claim 9, further comprising:
  separating, by the classical computing processor, electron-repulsion integrals associated with electrons in the molecular system into a short-range and a long-range.

15. A system, comprising:
  a classical computing processor that generates a density-functional theory determination based on input data associated with a molecular system, comprising:
    determining inactive long-range contributions of frozen orbitals of the molecular system to the density-functional theory determination, and
    determining inactive short-range contributions of the frozen orbitals to the density-functional theory determination; and
  a quantum computing processor that updates the density-functional theory determination by inputting a quantum density into the density-functional theory determination generated by the classical computing processor, wherein the quantum density is based on long-range contributions of unfrozen orbitals of the molecular system, and wherein the classical computing processor is operatively coupled to the quantum computing processor.

16. The system of claim 15, wherein the quantum computing processor iteratively communicates an updated density-functional theory determination to the first computing processor to perform an optimization of the updated density-functional theory determination.

17. The system of claim 15, wherein the classical computing processor separates the orbitals in the molecular system into the frozen orbitals and the unfrozen orbitals.

18. A computer-implemented method, comprising:
  employing, by a device operatively coupled to a processor, a classical computing processor to implement a density-functional theory determination based on input data associated with a molecular system, comprising:
    determining inactive long-range contributions of frozen electrons of the molecular system to the density-functional theory determination, and
    determining inactive short-range contributions of the frozen electrons to the density-functional theory determination;
  employing, by the device, a quantum computing processor to update the density-functional theory determination, resulting in an updated density-functional theory determination, wherein the quantum density is based on long-range contributions of unfrozen electrons of the molecular system; and
  employing, by the device, the classical computing processor to optimize the updated density-functional theory determination based on iterative density-functional theory-based embedding for quantum computing determinations.

19. The computer-implemented method of claim 18, further comprising employing, by the device, the classical computing processor to separate electrons in the molecular system into the frozen electrons and the unfrozen electrons.

20. The computer-implemented method of claim 18, wherein the density-functional theory determination comprises an active density matrix.

21. The computer-implemented method of claim 18, further comprising separating electron-repulsion integrals associated with electrons in the molecular system into a short-range and a long-range.

22. A device, comprising:
   a classical computing processor that generates a density-functional theory determination based on input data associated with a molecular system, comprising:
      determining inactive long-range contributions of frozen electrons of the molecular system to the density-functional theory determination, and
      determining inactive short-range contributions of the frozen electrons to the density-functional theory determination; and
   a quantum computing processor that updates the density-functional theory determination based on long-range contributions of unfrozen electrons of the molecular system, resulting in an updated density-functional theory determination,
   wherein the classical computing processor optimizes the updated density-functional theory determination based on iterative density-functional theory-based embedding for quantum computing determinations.

23. The device of claim 22, wherein the classical computing processor separates electrons in the molecular system into the frozen electrons and the unfrozen electrons.

24. The device of claim 22, wherein a quantity of qubits utilized by the quantum computing processor are mitigated.

25. The device of claim 22, wherein the classical computing processor separates electron-repulsion integrals associated with electrons in the molecular system into a short-range and a long-range.

* * * * *